US012670203B2

(12) United States Patent
Browder et al.

(10) Patent No.: US 12,670,203 B2
(45) Date of Patent: Jun. 30, 2026

(54) SYSTEM AND METHOD FOR GENERATING AN UPDATED TERMINAL NODE PROJECTION

(71) Applicant: Signet Health Corporation, North Richland Hills, TX (US)

(72) Inventors: Blake Browder, Dallas, TX (US); Joy Figarsky, Little Rock, AR (US)

(73) Assignee: BH Operations, LLC, North Richland Hills, TX (US)

( * ) Notice: Subject to any disclaimer, the term of this patent is extended or adjusted under 35 U.S.C. 154(b) by 0 days.

(21) Appl. No.: 19/193,453

(22) Filed: Apr. 29, 2025

(65) Prior Publication Data

US 2026/0147818 A1 May 28, 2026

Related U.S. Application Data

(63) Continuation of application No. 18/957,799, filed on Nov. 24, 2024, now Pat. No. 12,314,305.

(51) Int. Cl.
| | |
|---|---|
| *G06F 16/358* | (2025.01) |
| *G06F 16/3329* | (2025.01) |
| *G16H 40/20* | (2018.01) |

(52) U.S. Cl.
CPC ...... *G06F 16/358* (2019.01); *G06F 16/33295* (2025.01); *G16H 40/20* (2018.01)

(58) Field of Classification Search
CPC ......... G06N 20/00; G06N 3/08; G06N 3/045; G06F 40/30; G06F 16/285; G10L 15/063; G10L 15/16
See application file for complete search history.

(56) References Cited

U.S. PATENT DOCUMENTS

| | | | | |
|---|---|---|---|---|
| 11,100,289 | B1 * | 8/2021 | Kailasam | ................ G06F 40/30 |
| 11,145,395 | B1 * | 10/2021 | Mitchell | ................ G16H 40/67 |
| 11,460,973 | B1 * | 10/2022 | Mealin | ..................... G06N 3/09 |
| 11,600,380 | B2 | 3/2023 | Martindale et al. | |
| 11,646,105 | B2 | 5/2023 | Rumoro | |
| 2016/0048938 | A1 * | 2/2016 | Jones | ............... G06Q 10/06315 |
| | | | | 705/7.28 |
| 2020/0090034 | A1 | 3/2020 | Ramachandran et al. | |
| 2020/0184017 | A1 | 6/2020 | Batra et al. | |

(Continued)

FOREIGN PATENT DOCUMENTS

| | | |
|---|---|---|
| KR | 20210113042 A | 9/2021 |
| WO | 2022083140 A1 | 4/2022 |

*Primary Examiner* — Jakieda R Jackson
(74) *Attorney, Agent, or Firm* — CALDWELL LLC

(57) ABSTRACT

A system for generating an updated terminal node projection, wherein the system includes: at least a processor; and a memory communicatively connected to the at least a processor, wherein the memory contains instructions configuring the at least a processor to: receive a plurality of datasets, wherein each dataset of the plurality of datasets is associated with a terminal node; identify a terminal node projection as a function of the plurality of datasets; generate an entry criteria set as a function of the terminal node projection using a first machine-learning model; train a second machine-learning model configured to receive the entry criteria set as input; retrain the second machine-learning model; generate an updated terminal node projection as a function of the retrained second machine-learning model and the plurality of datasets.

20 Claims, 7 Drawing Sheets

(56)            References Cited

U.S. PATENT DOCUMENTS

| | | | |
|---|---|---|---|
| 2022/0121967 A1* | 4/2022 | Azizsoltani | G06N 5/025 |
| 2022/0138585 A1* | 5/2022 | Heilbroner | G06F 18/232 |
| | | | 706/15 |
| 2022/0229991 A1 | 7/2022 | Duong et al. | |
| 2022/0230000 A1 | 7/2022 | Jalaluddin et al. | |
| 2022/0335219 A1 | 10/2022 | Sengupta et al. | |
| 2022/0336088 A1* | 10/2022 | Thomas | G16H 50/20 |
| 2023/0072199 A1 | 3/2023 | Li | |
| 2023/0169393 A1 | 6/2023 | Niu et al. | |
| 2023/0185799 A1 | 6/2023 | Hoang et al. | |
| 2023/0214753 A1* | 7/2023 | Eidelman | G06N 5/02 |
| | | | 705/7.37 |
| 2023/0253100 A1 | 8/2023 | Caudill et al. | |
| 2024/0013318 A1 | 1/2024 | Moyerman et al. | |
| 2024/0028831 A1 | 1/2024 | Jain et al. | |
| 2024/0071598 A1 | 2/2024 | Neumann et al. | |
| 2024/0233952 A1* | 7/2024 | Morin | G16H 50/20 |
| 2024/0252048 A1* | 8/2024 | Tran | A61B 5/0538 |
| 2024/0370505 A1 | 11/2024 | Devaux et al. | |
| 2024/0395417 A1* | 11/2024 | Gada | G16H 50/30 |
| 2024/0420124 A1 | 12/2024 | Ramde et al. | |
| 2025/0078991 A1* | 3/2025 | de la Torre | G16H 40/20 |

* cited by examiner

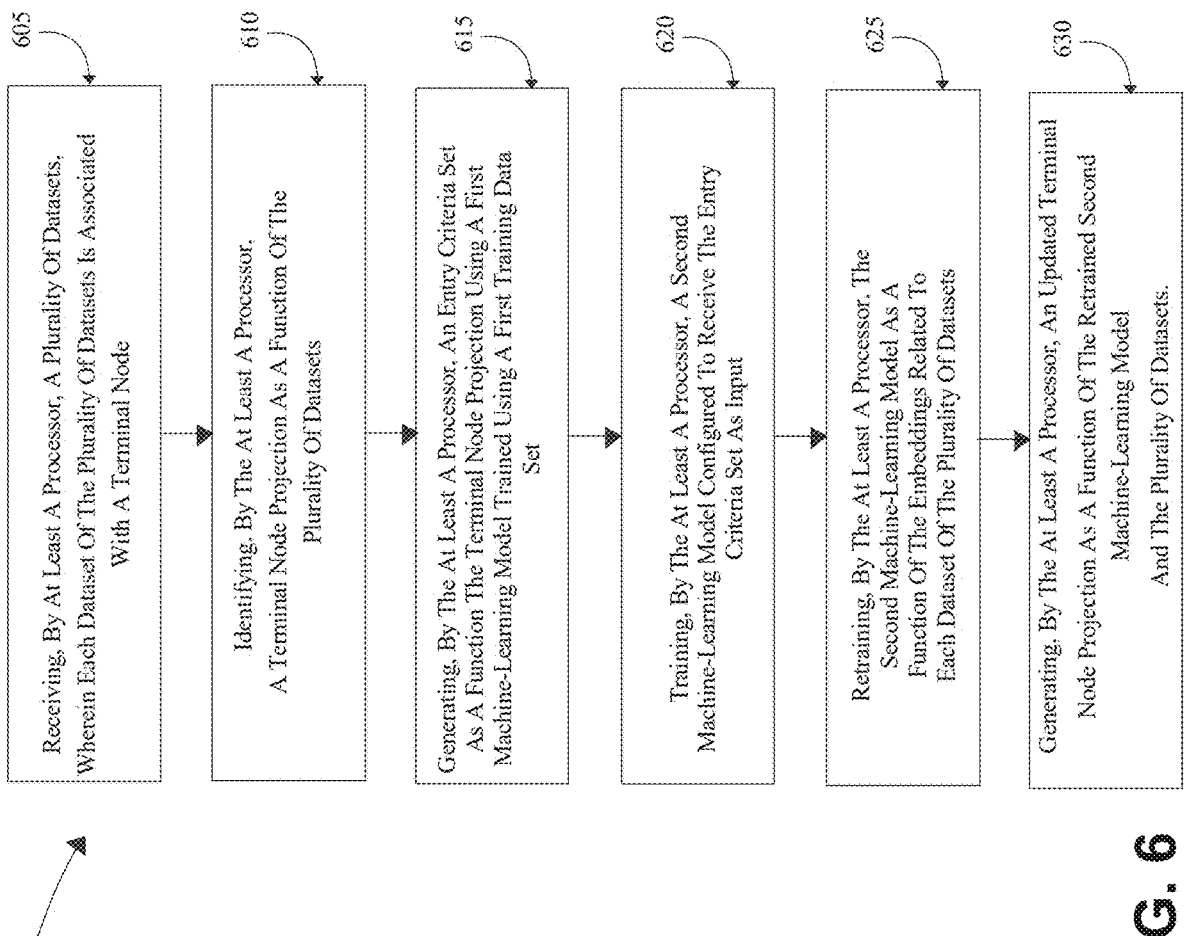

600

605
Receiving, By At Least A Processor, A Plurality Of Datasets, Wherein Each Dataset Of The Plurality Of Datasets Is Associated With A Terminal Node 610
Identifying, By The At Least A Processor, A Terminal Node Projection As A Function Of The Plurality Of Datasets 615
Generating, By The At Least A Processor, An Entry Criteria Set As A Function The Terminal Node Projection Using A First Machine-Learning Model Trained Using A First Training Data Set 620
Training, By The At Least A Processor, A Second Machine-Learning Model Configured To Receive The Entry Criteria Set As Input 625
Retraining, By The At Least A Processor, The Second Machine-Learning Model As A Function Of The Embeddings Related To Each Dataset Of The Plurality Of Datasets 630
Generating, By The At Least A Processor, An Updated Terminal Node Projection As A Function Of The Retrained Second Machine-Learning Model And The Plurality Of Datasets.

FIG. 6

SYSTEM AND METHOD FOR GENERATING AN UPDATED TERMINAL NODE PROJECTION

CROSS-REFERENCE TO RELATED APPLICATIONS

This application is a continuation of Non-provisional application Ser. No. 18/957,799, filed on Nov. 24, 2024, and entitled "SYSTEM AND METHOD FOR GENERATING AN UPDATED TERMINAL NODE PROJECTION," the entirety of which is incorporated herein by reference.

FIELD OF THE INVENTION

The present invention generally relates to the field of data processing. In particular, the present invention is directed to a system and method for generating an updated terminal node projection.

BACKGROUND

Current technological systems lack the ability to efficiently process and interpret unstructured data. Unstructured data, such as text documents, emails, and multimedia files, often contains valuable insights but is complex and varied in format. Traditional models struggle with this diversity and typically cannot accurately analyze or organize such data without extensive preprocessing.

SUMMARY OF THE DISCLOSURE

In an aspect, a system for generating an updated terminal node projection, wherein the system includes: at least a processor; and a memory communicatively connected to the at least a processor, wherein the memory contains instructions configuring the at least a processor to: receive a plurality of datasets, wherein each dataset of the plurality of datasets is associated with a terminal node; identify a terminal node projection as a function of the plurality of datasets, wherein identifying the terminal node projection comprises classifying each dataset of the plurality of datasets using natural language processing, wherein classification of each dataset of the plurality of datasets generates embeddings related to each dataset of the plurality of datasets; generate an entry criteria set as a function of the terminal node projection and generate an updated terminal node projection as a function of a trained machine-learning model, the entry criteria set, and the plurality of datasets.

In another aspect, a method for generating an updated terminal node projection, wherein the system includes: at least a processor; and a memory communicatively connected to the at least a processor, wherein the memory contains instructions configuring the at least a processor to: receiving, by at least a processor, a plurality of datasets, wherein each dataset of the plurality of datasets is associated with a terminal node; identifying, by the at least a processor, a terminal node projection as a function of the plurality of datasets, wherein identifying the terminal node projection comprises classifying each dataset of the plurality of datasets using natural language processing, wherein classification of each dataset of the plurality of datasets generates embeddings related to each dataset of the plurality of datasets; generating, by the at least a processor, an entry criteria set as a function of the terminal node projection and generating, by the at least a processor, an updated terminal node projection as a function of a trained machine-learning model, the entry criteria set, and the plurality of datasets.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 6 is a block diagram of an exemplary embodiment of a method for generating an updated terminal node projection.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an updated terminal projection. In an embodiment, a system for generating an updated terminal node projection, wherein the system includes: at least a processor; and a memory communicatively connected to the at least a processor, wherein the memory contains instructions configuring the at least a processor to: receive a plurality of datasets, wherein each dataset of the plurality of datasets is associated with a terminal node; identify a terminal node projection as a function of the plurality of datasets, wherein identifying the terminal node projection comprises classifying each dataset of the plurality of datasets using natural language processing, wherein classification of each dataset of the plurality of datasets generates embeddings related to each dataset of the plurality of datasets; generate an entry criteria set as a function of the terminal node projection using a first machine-learning model trained using a first training data set configured to correlate the at least a plurality of datasets correlated to the entry criteria set; train a second machine-learning model configured to receive the entry criteria set as input, wherein the second machine-learning model is trained using a second training data set configured to correlate the entry criteria set to a terminal node; retrain the second machine-learning model as a function of the embeddings related to each dataset of the plurality of datasets; generate an updated terminal node projection as a function of the retrained second machine-learning model and the plurality of datasets.

Exemplary embodiments illustrating aspects of the present disclosure are described below in the context of several specific examples.

Figure 1:
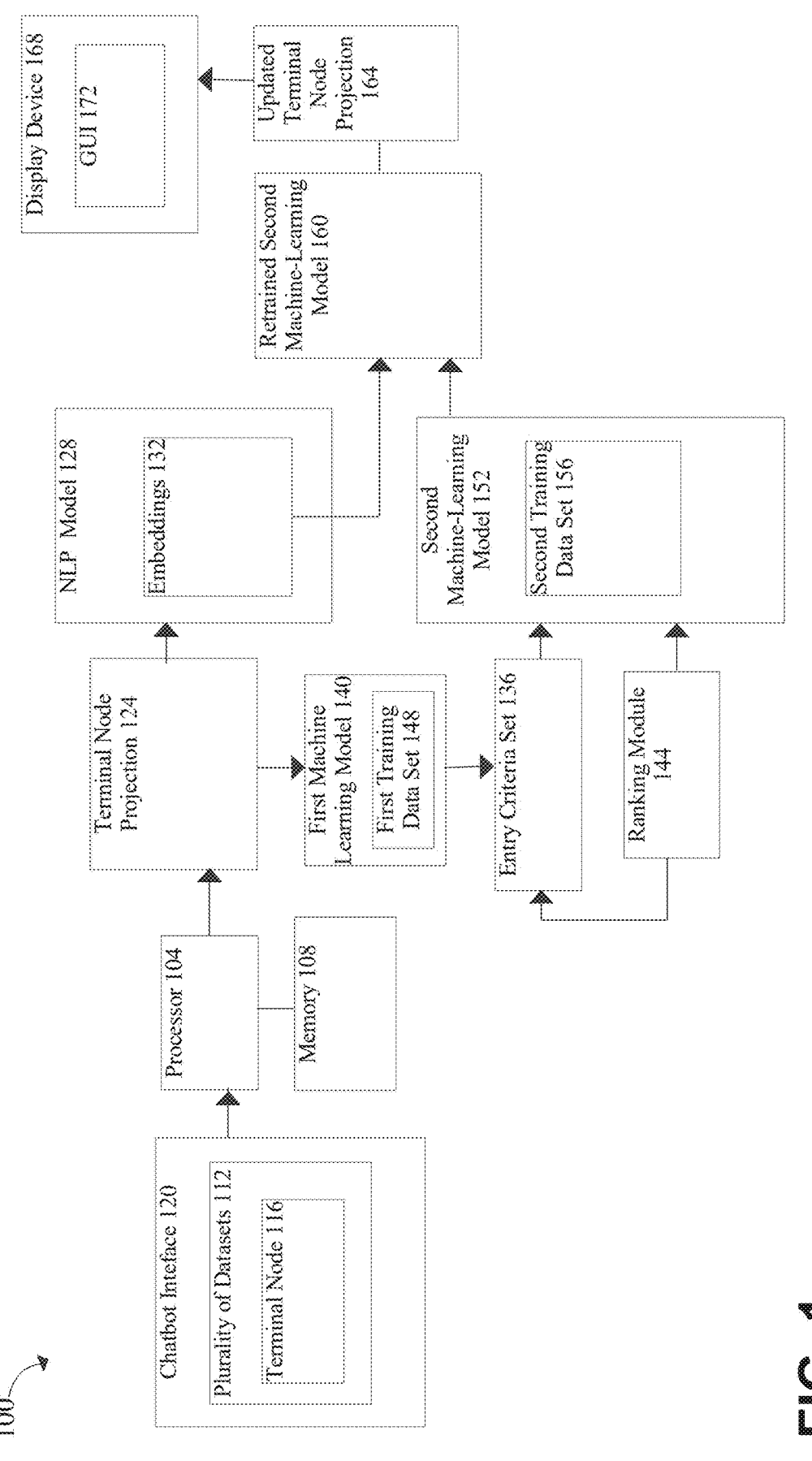
FIG. 1 is a flow diagram illustrating a system for generating an updated terminal node projection.

Referring now to FIG. 1, an exemplary embodiment of a system that generating an updated terminal node projection is illustrated. System 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor 104. In one or more embodiments, data is transferred from secondary to primary memory wherein processor 104 may access the information from primary memory.

Still referring to FIG. 1, system 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine-learning may be performed by network server, wherein data is transmitted to server, processed and transmitted back to computing device. In one or more embodiments, server may be configured to perform one or more processes as described below to allow for increased computational power and/or decreased power usage by the system computing device. In one or more embodiments, computing device may transmit processes to server wherein computing device may conserve power or energy.

Further referring to FIG. 1, system 100 may include any "computing device" as described in this disclosure, including without limitation a microcontroller, microprocessor, digital signal processor (DSP) and/or system on a chip (SoC) as described in this disclosure. System 100 may include, be included in, and/or communicate with a mobile device such as a mobile telephone or smartphone. System 100 may include a single computing device operating independently, or may include two or more computing devices operating in concert, in parallel, sequentially or the like; two or more computing devices may be included together in a single computing device or in two or more computing devices. System 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. System 100 may include one or more computing devices dedicated to data storage, security, distribution of traffic for load balancing, and the like. System 100 may distribute one or more computing tasks as described below across a plurality of computing devices of computing device, which may operate in parallel, in series, redundantly, or in any other manner used for distribution of tasks or memory between computing devices. System 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. In a non-limiting embodiment, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 may be configured to receive a plurality of datasets 112, wherein each dataset of the plurality of datasets is associated with a terminal node 116. As used herein, a "plurality of datasets" refers to multiple sets of data inputs, each containing distinct information relevant to a specific area, category, or instance being analyzed. The plurality of datasets 112 may include structured or unstructured data and are associated with different conditions, attributes, or inputs required to make informed decisions or classifications within the system. In a non-limiting embodiment, plurality of datasets 112 may include data relating to admission decisions related to prospective patients in key hospitals operating in the behavioral health and rehab spaces. In another non-limiting embodiment, the plurality of datasets 112 may include patient cohort data, hospital data, admission criteria, and admission outcomes. In an embodiment, each dataset of the plurality of datasets may relate to a specific patient, hospital sect, patient demographic, and the like. As used herein, a "terminal node" represents a final output or endpoint in a classification, decision-making, or data processing pathway within a system. In a non-limiting embodiment, terminal node 116 may represent an admission outcome, indicating the final decision or classification point regarding an individual's eligibility, acceptance or status within an admission process. Terminal node 116 may embody various specific results, such as "accepted," "waitlisted," "rejected," or "deferred," based on the plurality of data 112 processed throughout the system 100.

Continuing reference to FIG. 1, in an embodiment, plurality of datasets 112, may be received through a chatbot interface 120. As used herein, a "chatbot interface" refers to a user interface that allows users to interact with system 100 through natural language input, typically in the form of text or speech. For instance, clinical staff might use the chatbot interface to inquire about admission availability for a specific patient group, or request updates on treatment progression metrics. The chatbot interface leverages Natural Language Processing (NLP), a subfield of artificial intelligence dedicated to enabling systems to interpret, understand, and generate human language. NLP involves multiple layers of text analysis, such as tokenization, part-of-speech tagging, syntactic parsing, and semantic analysis. In an advanced embodiment, the chatbot interface may incorporate sophisticated NLP techniques, including word embeddings (e.g., Word2Vec, GloVe), which transform words into vector representations to capture contextual meaning, and transformer-based architectures (e.g., BERT, GPT), which enhance the system's ability to process complex queries that rely on contextual relationships between words. For example, if a user queries, "What is the admission status for patients in the psychiatric unit?" the transformer models can interpret that the query requires a response filtered by both patient type and hospital unit. Additionally, entity recognition may be applied within the NLP models to identify key elements such as patient names, medical terms, and numerical statistics within the data. For example, in a query like "Show bed availability for adolescent patients in rehab," the system may recognize "bed availability," "adolescent patients," and "rehab" as essential entities. Moreover, intent recognition classifies the purpose behind the user's input (e.g., requesting information, initiating a decision, or performing an action), allowing system 100 to interpret that the user is asking for availability statistics specific to the rehabilitation unit. The response may be structured in a conversational format, simulating a human-like interaction to enhance usability and user experience.

Still referring to FIG. 1, chatbot interface 120 may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, diagnosis reports, admission outcomes, and the like. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine-learning process. In some embodiments, generally training an LLM may be performed using an unsupervised machine-learning process. As a non-limiting example, specific training set may include information from a database. As a non-limiting example, specific training set may include text related to the users such as user specific data for electronic records correlated to examples of outputs. In an embodiment, training one or more machine-learning models may include setting the parameters of the one or more models (weights and biases) either randomly or using a pretrained model. Generally training one or more machine-learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "How many beds", then it may be highly likely that the word "are available" will come next. An LLM may output such predictions by ranking words by likelihood or a prompt parameter. For the example given above, an LLM may score "you" as the most likely, "you're" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. A query vector may include an entity's learned representation for comparison to determine attention score. A key vector may include an entity's learned representation for determining the entity's relevance and attention weight. A value vector may include data used to generate output representations. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with plurality of datasets 112.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Continuing reference to FIG. 1, at least a processor 104 may be configured to identify a terminal node projection 124 as a function of the plurality of datasets 112. As used herein, a "terminal node projection" refers to a predicted output generated by system 100 based on aggregated analysis of the plurality of datasets 112. In an embodiment, terminal node projection 124 may serve as a predictive classification or decision indicator aligned with specific criteria and thresholds, that may be informed by historical data, cluster analysis, and the like. In an embodiment, terminal node projection 124 may be used to predict whether a specific patient will be "accepted," "waitlisted," "rejected," or "deferred" based on real-time data points and historical trends in patient admissions. This projection could consider factors such as available bed capacity, patient demographics, admission urgency, and historical acceptance rates for similar cases. In another non-limiting embodiment, terminal node projection 124 may be used to indicate that a patient is likely to be waitlisted. This projection might apply to cases where admission demand exceeds current capacity, but the patient's condition qualifies them for consideration once a space becomes available. The terminal node projection 124 could also consider historical waitlist durations for similar patient profiles, providing an estimated wait time. In another non-limiting embodiment, the terminal node projection 124 may be used to estimate the expected length of stay for each admitted patient. For instance, patients admitted for routine rehabilitation might receive a projection indicating a "short-term stay" classification, whereas more complex cases may result in a "long-term stay" projection. This outcome helps allocate resources by predicting discharge timelines and bed availability. In another non-limiting embodiment, terminal node projection 124 may be used to project the urgency of a new admission request. For example, patients requiring immediate intervention due to acute mental health crises might receive an "urgent" admission projection, while stable cases could receive a "routine" projection. This projection aids in triaging and prioritizing admissions based on the projected urgency.

Continuing reference to FIG. 1, The plurality of datasets 112 may contain image documentation, including patient history, hospital information, admission outcomes, and similar records. In an embodiment, optical character recognition (OCR) may be used to convert information contained within the image documentation in the plurality of datasets 112 into a machine-readable format. This conversion may allow the system to process and analyze textual data embedded in images, making it accessible for further data extraction, analysis, and predictive modeling. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine-learning processes. In some cases, intelligent word recognition (IWR) may recognize written text, one word at a time, for instance by employing machine-learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 3-5. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 3-5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Continuing reference to FIG. 1, identifying the terminal node projection 124 may include classifying each dataset of the plurality of datasets using a natural language processing (NLP) model 128, wherein classification of each dataset of the plurality of datasets generates embeddings 132 related to each dataset of the plurality of datasets. Embeddings may include dense vector representations that capture semantic relationships and contextual information within the data, allowing the system to encode the meaning of each dataset in a numerical form. For instance, if the dataset includes patient admission notes, the NLP model 128 may generate embeddings that capture critical elements, such as diagnosis terms, treatment history, and key symptoms. This embedding generation may use techniques such as word embeddings (e.g., Word2Vec, GloVe) or contextual embeddings derived from transformer-based models (e.g., BERT, GPT), which allow the system to consider the relationships between words and phrases in each dataset. For example, datasets with similar embeddings related to "urgent psychiatric care" may be classified toward a terminal node projection 124 indicating an immediate admission outcome, while datasets with embeddings suggesting lower acuity or routine needs could be classified toward a standard or deferred admission projection. In another non-limiting embodiment, for a plurality of datasets 112 containing patient intake notes, NLP techniques may identify keywords and patterns related to a mental health crisis, such as "suicidal ideation," "severe depression," or "psychotic episode." The embeddings generated from these terms may classify the dataset toward a high-priority admission terminal node projection, indicating that immediate inpatient care is necessary. In another non-limiting embodiment, using NLP model 128 on datasets with previous discharge notes, follow-up reports, and patient histories, the system may generate embeddings that capture patterns indicating a high likelihood of readmission, such as phrases like "non-compliant with medication" or "lack of support at home." These embeddings may align the dataset with a terminal node projection 124 that categorizes the patient as "high-risk for readmission." In an embodiment, NLP model 128 may utilize at least a machine-learning algorithm to classify text from the plurality of datasets 112 into categories. In an embodiment, these categories may include sentiment, topic, intent, and the like. The machine-learning model may be trained using training data configured to correlate historical text classifications, example textual classifications, and the like to historical categories, example categories, and the like. In another embodiment, the NLP model 128 may analyze datasets with historical discharge notes, follow-up reports, and patient histories. Through this, embeddings may reveal patterns indicating a high risk of readmission, such as phrases like "non-compliant with medication" or "limited family support." These embeddings can align the dataset with a terminal node projection 124 categorizing the patient as "high-risk for readmission." In an embodiment, the terminal node projection may serve as a predictive categorization based on recurring patterns of prior readmission cases, essentially forecasting the likely need for additional intervention.

Continuing reference to FIG. 1, at least a processor 104 may be configured to generate an entry criteria set 136 as a function of the terminal node projection 124 using a first machine-learning model 140. As used herein, an "entry criteria set" refers to a defined collection of conditions, parameters, or thresholds that must be met for a specific process to proceed within a system. In an embodiment, entry criteria set 136 may include data related to an admission criteria set, which may define requirements and eligibility standards that should be met for a patient to be considered for admission to a particular facility or program. In an embodiment, entry criteria set 136 may include various factors, such as medical diagnoses, condition severities, treatment histories, age ranges, financial or insurance qualifications, and the like. In another non-limiting embodiment, in a behavioral health admission process, entry criteria set 136 may include data points related to severity of mental health symptoms, recent history of hospitalizations, need for specialized services, and the like. Entry criteria set 136 may be designed to align incoming cases with the appropriate resources and facilities, ensuring that each patient meets the necessary conditions for admission based on their dataset. In an embodiment, a ranking module 144 may be configured to rank the weights of the entry criteria set. The ranking module 144 may be configured to generate an ordered hierarchy based on the relative importance or priority of each criterion within the entry criteria set 136. The ranking module 144 may assign a weight or value to each entry criterion of the entry criteria set 136, reflecting its significance in the overall admission or classification process. For instance, in a healthcare admissions model, the ranking module 144 might assign higher weights to critical criteria such as the severity of the patient's condition, immediate treatment needs, or availability of specialized resources, while assigning lower weights to less critical factors like patient demographic details or non-essential preferences. For example, in a rehabilitation facility, the module might rank "mobility limitations" and "need for intensive therapy" as top-weighted criteria, since these factors significantly impact resource allocation and care requirements. Conversely, a factor such as "distance from facility" might receive a lower weight, as it is less critical in determining admission eligibility. In an embodiment, historical data can be analyzed to identify which criteria have had the most significant impact on the entry criteria set 136 (e.g., successful admissions, reduced readmissions, patient recovery times). By analyzing correlations and statistical significance, weights can be assigned to each criterion based on its influence on these outcomes. Techniques such as correlation coefficients, chi-square tests, or regression analysis may be used to determine how strongly each criterion correlates with desirable admission outcomes. The ranking module 144 may operate using algorithms that consider various data-driven factors, such as historical admission patterns, clinical guidelines, or predictive analytic s, to determine which criteria should carry more influence in the decision-making process. Ranking module 144 may include a supervised machine-learning model configured to correlate entry criteria data to a ranking value. The supervised machine-learning model may be trained using training data including correlations between historical or example entry criteria data to historical or example ranking values. The supervised machine-learning model may be retrained as a function of user feedback on the accuracy of the output ranked values, where negative feedback indicates a poor correlation. In an embodiment, generating the entry criteria set 136 may include using a first machine-learning model 140 trained using a first training data set 148. The training data set may comprise exemplary dataset correlated to exemplary entry criteria. During training, the first machine-learning model may use labeled examples in the first training data set 148 to analyze which features or combinations of features are most predictive of qualifying for the entry criteria set 136. In an embodiment, the plurality of datasets 112 may include patient information, historical admission decisions, and treatment outcomes, and the first machine-learning model 140 may be configured learn to identify key patterns that align with successful admissions or eligibility criteria, such as specific diagnosis types, demographic information, severity scores, ranking criteria, and the like.

In an embodiment, the at least a processor 104 may be configured to apply a clustering algorithm to the entry criteria set 136. In an embodiment, the clustering algorithm is configured to correlate entry criteria sets as a function of an accuracy algorithm comprising a threshold calculation. In an embodiment, the clustering algorithm may be designed to identify natural groupings within the data, such as patients with similar admission requirements, treatment needs, or demographic profiles, and the like. In an embodiment, the clustering algorithm may be configured to correlate entry criteria sets 136 according to an accuracy algorithm that includes a threshold calculation. This accuracy algorithm may evaluate the quality and relevance of each cluster by setting a minimum threshold for inclusion, which can ensure that only entry criteria sets that meet a certain degree of similarity are grouped together. The threshold calculation may be based on distance metrics, such as Euclidean distance or cosine similarity, depending on the type of data and the clustering method used (e.g., k-means, hierarchical clustering, or DBSCAN). For instance, if entry criteria sets contain features such as condition severity, patient age, and required resources, the threshold calculation might set a maximum allowable distance between data points within a cluster, ensuring that only highly similar criteria sets are grouped together. Entry criteria sets that do not meet this similarity threshold may either be placed into separate clusters or flagged for further review.

Continuing reference to FIG. 1, at least a processor 104 may be configured to train a second machine-learning model 152 configured to receive the entry criteria set as input. In an embodiment, the second machine-learning model 152 may be configured to build on the entry criteria set, generated by the first machine-learning model 140. In an embodiment, the second machine-learning model 152 may be configured to take the entry criteria set 136 as input and map the entry criteria set to a terminal node. The second training dataset 156 includes correlations between configurations, such as the ranking module 144, of the entity criteria set 136 to the terminal node 124. For instance, if the entry criteria set indicates a high severity score with high-priority criteria based on diagnosis type and treatment urgency, the second model may learn to associate this with a high-priority admission terminal node, influenced by the weightings assigned by the ranking module 144. The ranking module's influence ensures that high-impact criteria play a larger role in the model's predictions, allowing the second machine-learning model 152 to distinguish between cases that qualify for immediate admission and those that do not meet critical thresholds. In an embodiment, the second machine-learning model may be trained as a function of example or historical cases where patients were rejected admission, but admitted at another hospital. This training approach allows the second machine-learning model to learn from situations where terminal nodes did not align at one facility but were suitable at another, thereby enabling it to better distinguish between cases based on subtle differences in eligibility criteria across hospitals or specialized facilities. For example, the second training data set 156 may include cases where a patient's medical condition was too complex for a general hospital, leading to an initial rejection, but later fit the criteria for a specialized hospital equipped to handle their specific needs. In such cases, the second-machine-learning model 152 would learn to recognize patterns associated with these types of outcomes, such as certain diagnosis codes, treatment requirements, or specific demographic factors that may influence suitability for different facilities. In an embodiment, the second machine-learning model 152 may be configured to combine embeddings 132 with additional contextual data from the plurality of datasets 112 to potentially create a more comprehensive input representation to enhance the second machine-learning model 152 predictive and classification capabilities. In addition to embeddings, the second machine-learning model 152 integrates contextual data from the datasets, such as timestamps, specific facility characteristics, admission policies, and environmental factors, that may influence outcomes but are not directly captured by the embeddings alone. For example, contextual data might include details on hospital resource availability, regional patient influx rates, or criteria variations specific to certain hospital departments. Contextual data can be updated frequently (e.g., changes in facility availability or patient influx), allowing the second machine-learning model 152 to adapt its projections dynamically.

Continuing reference to FIG. 1, at least a processor 104 may be configured to retrain the second machine-learning model 152 as a function of the embeddings 132 related to each dataset of the plurality of datasets 112. The retrained second machine-learning model 160 may use embeddings 132 to improve the model's ability to classify or predict terminal nodes, such as "accepted," "waitlisted," or "rejected," by adapting to the evolving patterns observed in new data. Each embedding may represent a compressed, yet information-filled, summary of the dataset's features, which may enable the second machine-learning model to learn more efficiently and update its decision-making criteria without requiring direct access to the raw data. During retraining, the processor may utilize embeddings derived from recent cases, which reflect current trends, changes in admission policies, or shifting resource availability, ensuring that the second machine-learning model stays relevant and accurate. Retraining the second machine-learning model with embeddings may may enhance the second machine-learning model's adaptability by allowing it to incorporate subtle, latent features within the datasets, which may enable it to respond to nuanced changes in patient profiles, treatment protocols, or facility requirements over time. In an embodiment, retraining the second machine-learning model may include an optimization protocol that may be used to refine the model's performance and efficiency based on updated data and embeddings. The optimization protocol may adjust various parameters within the model, such as learning rates, weight adjustments, or feature importance metrics, to enhance the model's ability to generalize and accurately map input data to terminal outcomes. The optimization protocol may also involve tuning hyperparameters, which may allow the second machine-learning model to identify the most relevant features in the embeddings, thereby reducing noise and focusing on high-impact data. Additionally, the optimization protocol may employ techniques such as gradient descent or stochastic optimization to iteratively minimize error rates, which may improve the model's predictive accuracy over time. This process may also involve regularization methods, which may prevent overfitting by constraining model complexity, ensuring that the retrained model remains robust when exposed to new datasets. In another non-limiting embodiment, the system 100 may be further configured to iteratively retrain the second machine-learning model 152 as a function of new embeddings generated from an updated plurality of datasets.

With continued reference to FIG. 1, at least a processor 104 may be configured to generate an updated terminal node projection 164 as a function of the retrained second machine-learning model 160 and the plurality of datasets 112. This updated terminal node projection 164 may reflect the most current predictions or classifications by taking into account the latest data trends, patient profiles, admission patterns, or treatment requirements identified in the plurality of datasets. In an embodiment, the retrained second machine-learning model 160 may analyze each dataset within the plurality of datasets 112, identifying critical features and contextual information to generate a terminal node projection that more accurately reflects the present needs or classifications within the system. In a non-limiting embodiment, if the plurality of datasets 112 includes newly admitted patient profiles or recently modified admission criteria, the retrained model may apply this information to determine whether a new patient should be classified as "accepted," "waitlisted," or "rejected," reflecting the updated admission framework. In an embodiment, the updated terminal node projection 164 may include a comparison between the projected terminal node and an analysis of the entry criteria set cross-referenced with the plurality of datasets. In an embodiment, at least a processor 104 may cross-reference elements within the entry criteria set 136, such as patient demographics, historical admission trends, or facility requirements, against current data within the plurality of datasets 112. This cross-referencing may reveal any discrepancies or areas where the updated terminal node projection 164 might differ from terminal node projections 124. In a non-limiting embodiment, the updated terminal node projection indicates a patient should be "accepted" based on an optimal match to entry criteria, then the cross-reference with historical data may confirm that similar patients were admitted under analogous conditions, reinforcing the validity of the terminal node projection 124. Conversely, if the comparison suggests deviations from past terminal nodes or entry criteria sets, the model may flag this for further review or adjustment. In an embodiment, updated terminal node projection 164 may be used to iteratively retrain first machine-learning model 140 or second machine-learning model 152. In another embodiment, updated terminal node projection 164 may be generated as a function of user feedback regarding the accuracy of terminal node projection 124. The system 100 may use this feedback to refine and retrain the second machine-learning model 152. In an embodiment, if multiple users indicate that certain types of patient profiles were inaccurately projected as "rejected" but were ultimately "accepted," the second machine-learning model 152 may adjust the underlying criteria or weightings to correct these patterns. This process may involve increasing the second-machine-learning model's sensitivity to specific entry criteria or contextual features highlighted by user feedback, such as severity scores or resource availability.

Continuing reference to FIG. 1, at least a processor 104 may be further configured to display, at a display device 168, the updated terminal node projection 164. In an embodiment, display device 168 may include graphical user interface 172, which may be designed to visually present the terminal node projection in an accessible and user-friendly format. The GUI 172 may display the updated terminal node projection 164 as an interactive component, allowing users to view detailed information or analyze underlying factors that contributed to the projection. Display device 168 may be configured to include visual indicators, such as color-coded statuses, icons, or progress bars, that may help users quickly interpret the projection outcome. Additionally, the GUI 172 may provide options for users to interact with the projection, such as filtering, sorting, or drilling down into specific entry criteria that informed the projection. These features may be customizable, depending on the user's role or requirements.

Figure 2:
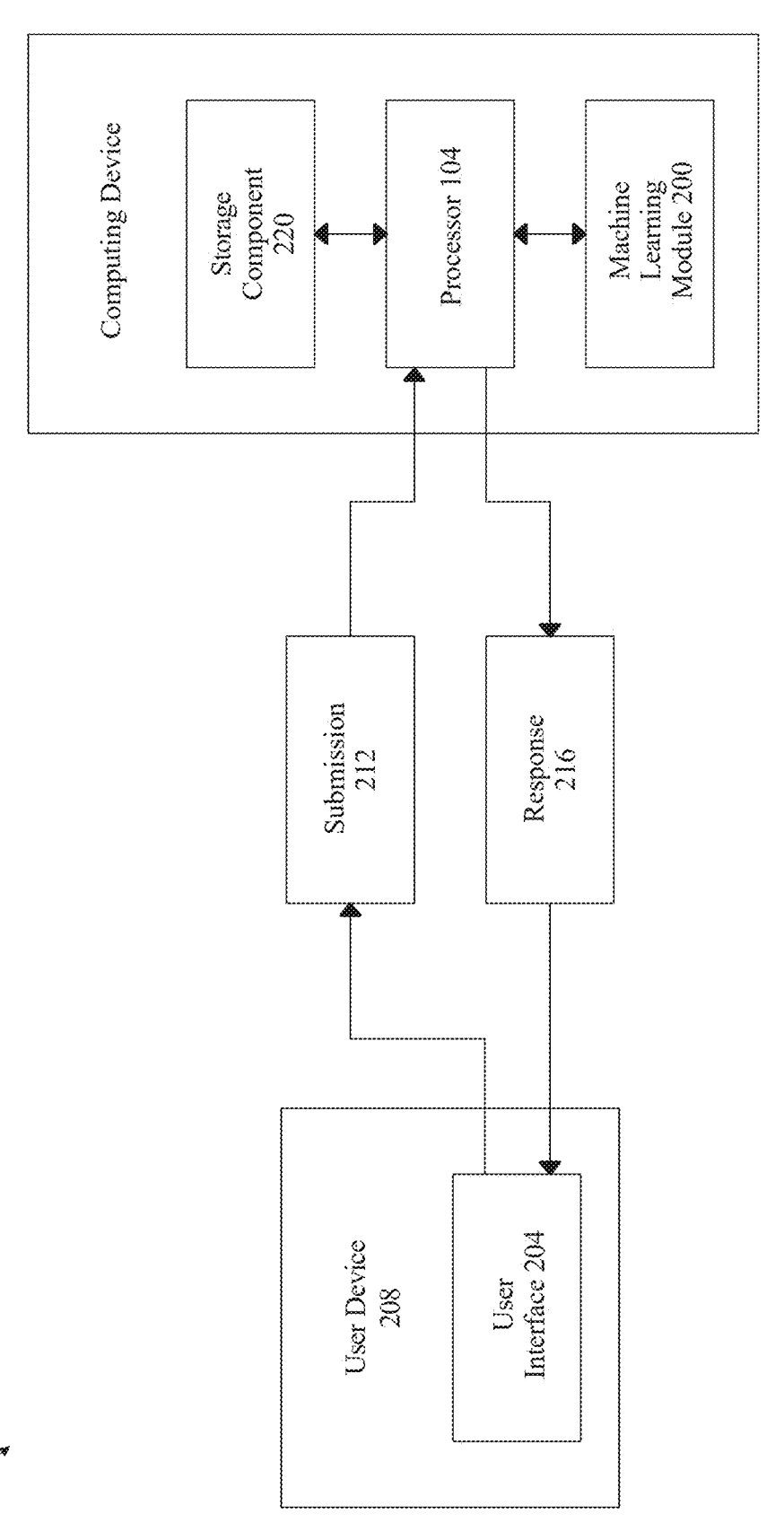
FIG. 2 is an exemplary embodiment of a chatbot system.

Referring to FIG. 2, a chatbot system 200 is schematically illustrated. According to some embodiments, a user interface 204 may be communicative with a computing device 208 that is configured to operate a chatbot. In some cases, user interface 204 may be local to computing device 208. Alternatively or additionally, in some cases, user interface 204 may remote to computing device 208 and communicative with the computing device 208, by way of one or more networks, such as without limitation the internet. Alternatively or additionally, user interface 204 may communicate with user device using telephonic devices and networks, such as without limitation fax machines, short message service (SMS), or multimedia message service (MMS). Commonly, user interface communicates with computing device 208 using text-based communication, for example without limitation using a character encoding protocol, such as American Standard for Information Interchange (ASCII). Typically, a user interface 204 conversationally interfaces a chatbot, by way of at least a submission 212, from the user interface 204 to the chatbot, and a response 216, from the chatbot to the user interface 204. In many cases, one or both of submission 212 and response 216 are text-based communication. Alternatively or additionally, in some cases, one or both of submission 212 and response 216 are audio-based communication.

Continuing in reference to FIG. 2, a submission 212 once received by computing device 208 operating a chatbot, may be processed by a processor 220. In some embodiments, processor 220 processes a submission 212 using one or more of keyword recognition, pattern matching, and natural language processing. In some embodiments, processor employs real-time learning with evolutionary algorithms. In some cases, processor 220 may retrieve a pre-prepared response from at least a storage component, based upon submission 212. Alternatively or additionally, in some embodiments, processor 220 communicates a response 216 without first receiving a submission 212, thereby initiating conversation. In some cases, processor 220 communicates an inquiry to user interface 204; and the processor is configured to process an answer to the inquiry in a following submission 212 from the user interface 204. In some cases, an answer to an inquiry present within a submission 212 from a user device may be used by computing device as an input to another function, for example without limitation terminal node projection 124 or updated terminal node projection 164.

Figure 3:
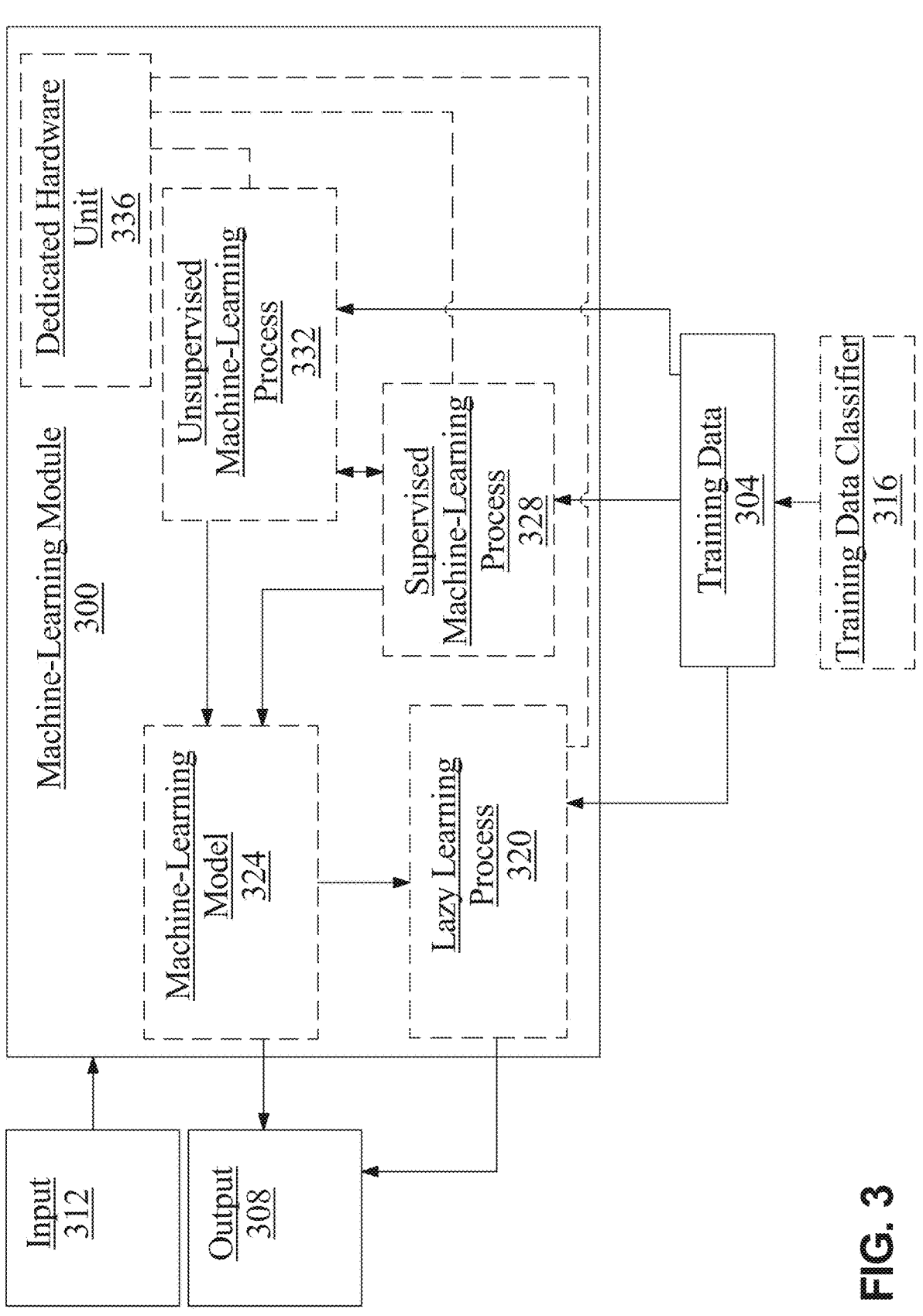
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. In a non-limiting embodiment, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; In a non-limiting embodiment, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, In a non-limiting embodiment by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; In a non-limiting embodiment, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, In a non-limiting embodiment, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs such as user input and plurality of command input event handlers and outputs such as optimization datum.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to categories of historical reference data and categories of historical plurality of command input event handlers.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. In a non-limiting embodiment, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, In a non-limiting embodiment, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. In a non-limiting embodiment, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, in a non-limiting embodiment, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. In a non-limiting embodiment, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, In a non-limiting embodiment, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. In a non-limiting embodiment, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. In a non-limiting embodiment, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. In a non-limiting embodiment, a computing device, processor, and/or module may convert a smaller number of units, such as in a low pixel count image, into a desired number of units, In a non-limiting embodiment by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, In a non-limiting embodiment by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, In a non-limiting embodiment as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, In a non-limiting embodiment using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. In a non-limiting embodiment, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. In a non-limiting embodiment, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. In a non-limiting embodiment, a supervised learning algorithm may include user input and plurality of command input event handlers as described above as inputs, optimization datum as outputs, and a scoring function representing a desired form of relationship to be detected between inputs and outputs; scoring function may, In a non-limiting embodiment, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. In a non-limiting embodiment, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, In a non-limiting embodiment, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. In a non-limiting embodiment, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, system, system and/or module. In a non-limiting embodiment, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, system, and/or method described in this disclosure; such examples may be modified and/or labeled according to user feedback or other processes to indicate desired results, and/or may have actual or measured results from a process being modeled and/or predicted by system, module, machine-learning model or algorithm, system, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, In a non-limiting embodiment, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, system, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
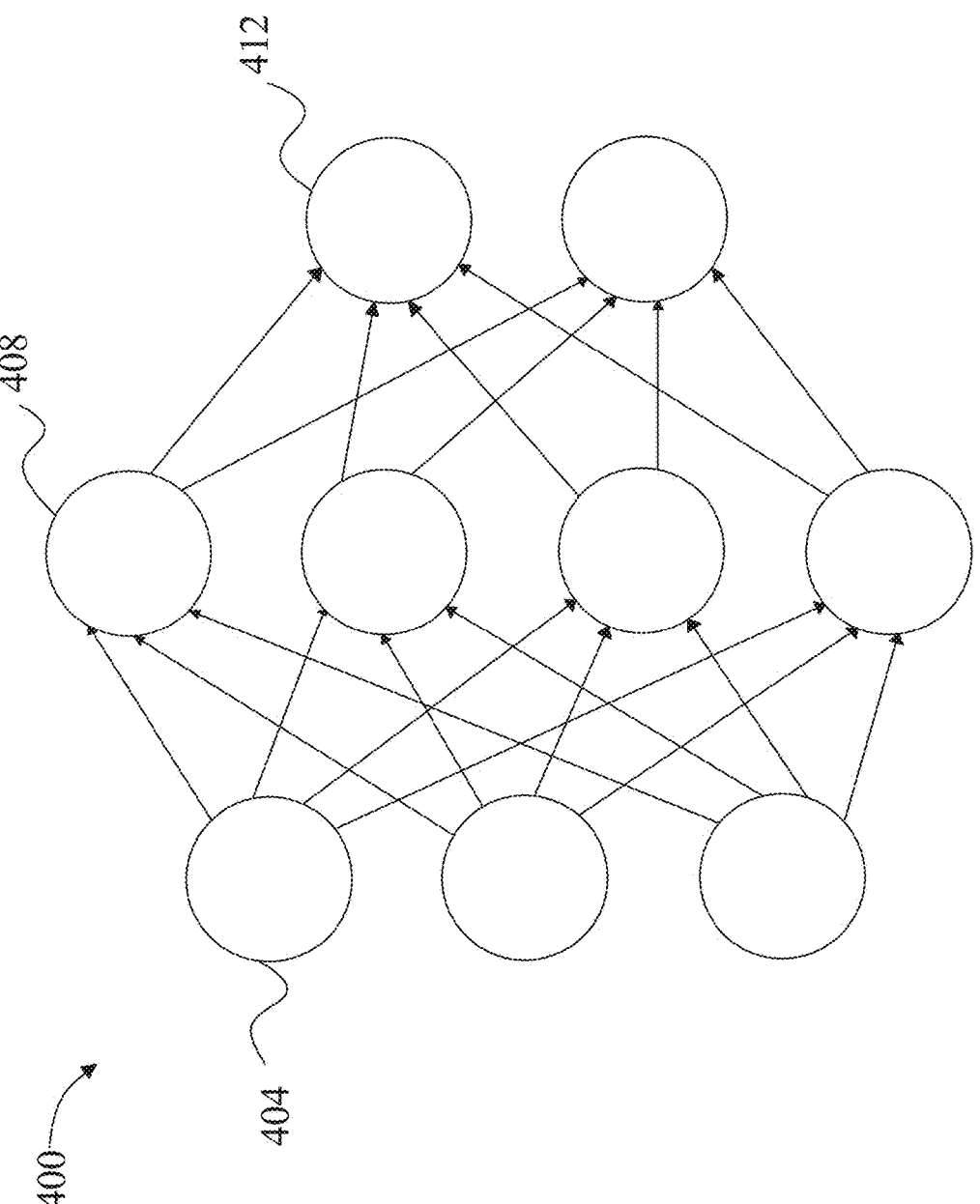
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
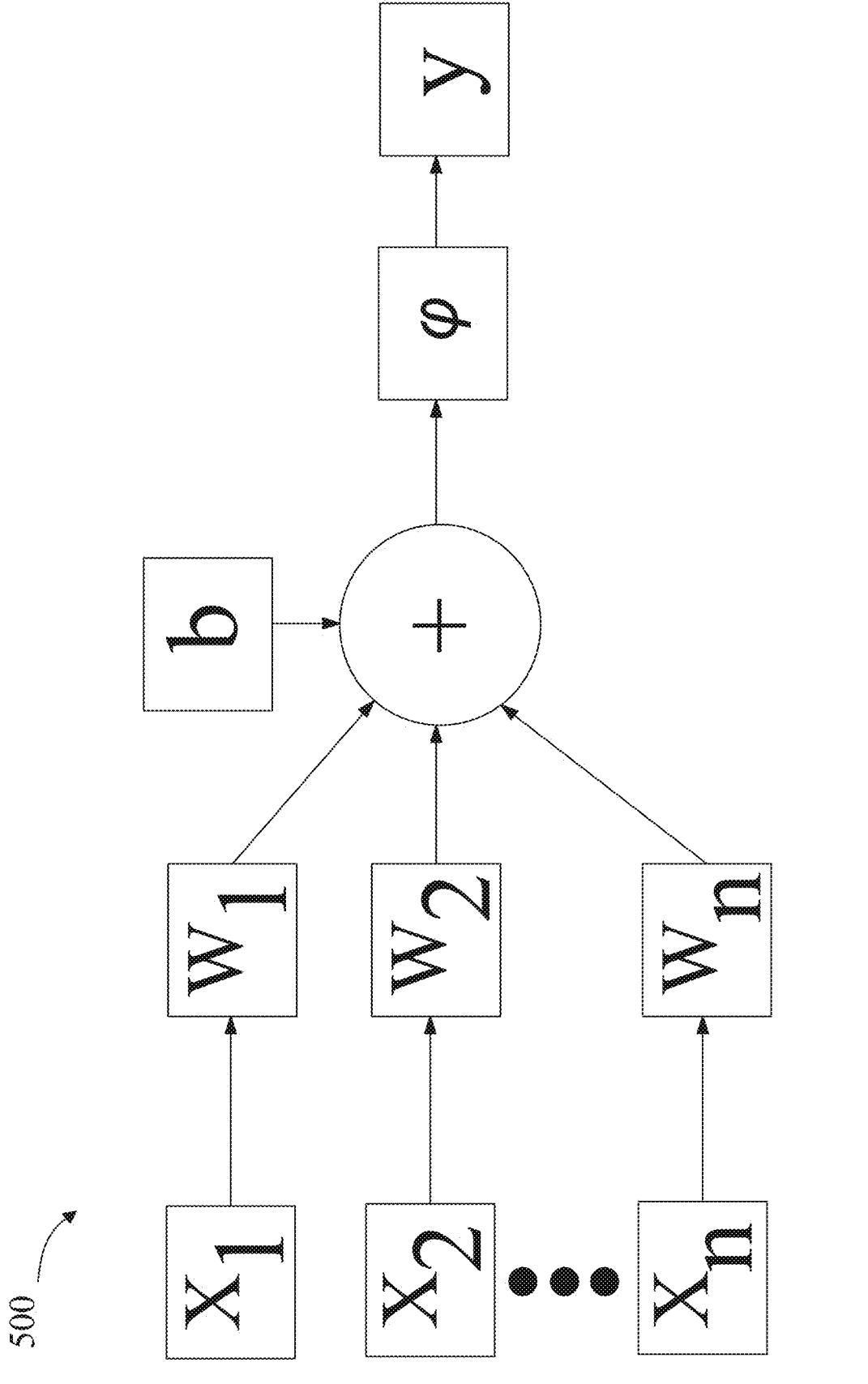
FIG. 5 is a diagram of an exemplary embodiment of a node of a neural network.

Referring now to FIG. 5, an exemplary embodiment of a node 500 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$, (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, In a non-limiting embodiment by the corresponding weight having a large numerical value, and/or a "inhibitory," indicating it has a weak effect influence on the one more inputs y, In a non-limiting embodiment by the corresponding weight having a small numerical value. The values of weights $w_i$ may be determined by training a neural network using training data, which may be performed using any suitable process as described above.

Now referring to FIG. 6, a method for generating an updated terminal node projection is illustrated. At step 605, method 600 includes receiving, by at least a processor, a plurality of datasets, wherein each dataset of the plurality of datasets is associated with a terminal node. This may be implemented with reference to FIGS. 1-5.

Still referring to FIG. 6, at step 610, method 600 includes identifying, by the at least a processor, a terminal node projection as a function of the plurality of datasets, wherein identifying the terminal node projection comprises classifying each dataset of the plurality of datasets using natural language processing model, wherein classification of each dataset of the plurality of datasets generates embeddings related to each dataset of the plurality of datasets. In an embodiment, generating an entry criteria set comprises a ranking module configured to rank the weights of each entry criterion of the entry criteria set. This may be implemented with reference to FIGS. 1-5.

Still referring to FIG. 6, at step 615, method 600 includes generating, by the at least a processor, an entry criteria set as a function the terminal node projection using a first machine-learning model trained using a first training data set configured to correlate the at least a plurality of datasets correlated to the entry criteria set. This may be implemented with reference to FIGS. 1-5.

Still referring to FIG. 6, at step 620, method 600 includes training, by the at least a processor, a second machine-learning model configured to receive the entry criteria set as input, wherein the second machine-learning model is trained using a second training data set configured to correlate the entry criteria set to the terminal node. In an embodiment, the second machine-learning model is configured to combine the embeddings of the plurality of datasets with contextual data from the plurality of datasets, retraining the second machine-learning model comprises an optimization protocol, and system is further configured to iteratively retrain the second machine-learning model as a function of new embeddings generated from an updated plurality of datasets. This may be implemented with reference to FIGS. 1-5.

Still referring to FIG. 6, at step 625, method 600 includes retraining, by the at least a processor, the second machine-learning model as a function of the embeddings related to each dataset of the plurality of datasets. This may be implemented with reference to FIGS. 1-5.

Still referring to FIG. 6, at step 630, method 600 includes generating, by the at least a processor, an updated terminal node projection as a function of the retrained second machine-learning model and the plurality of datasets. This may be implemented with reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
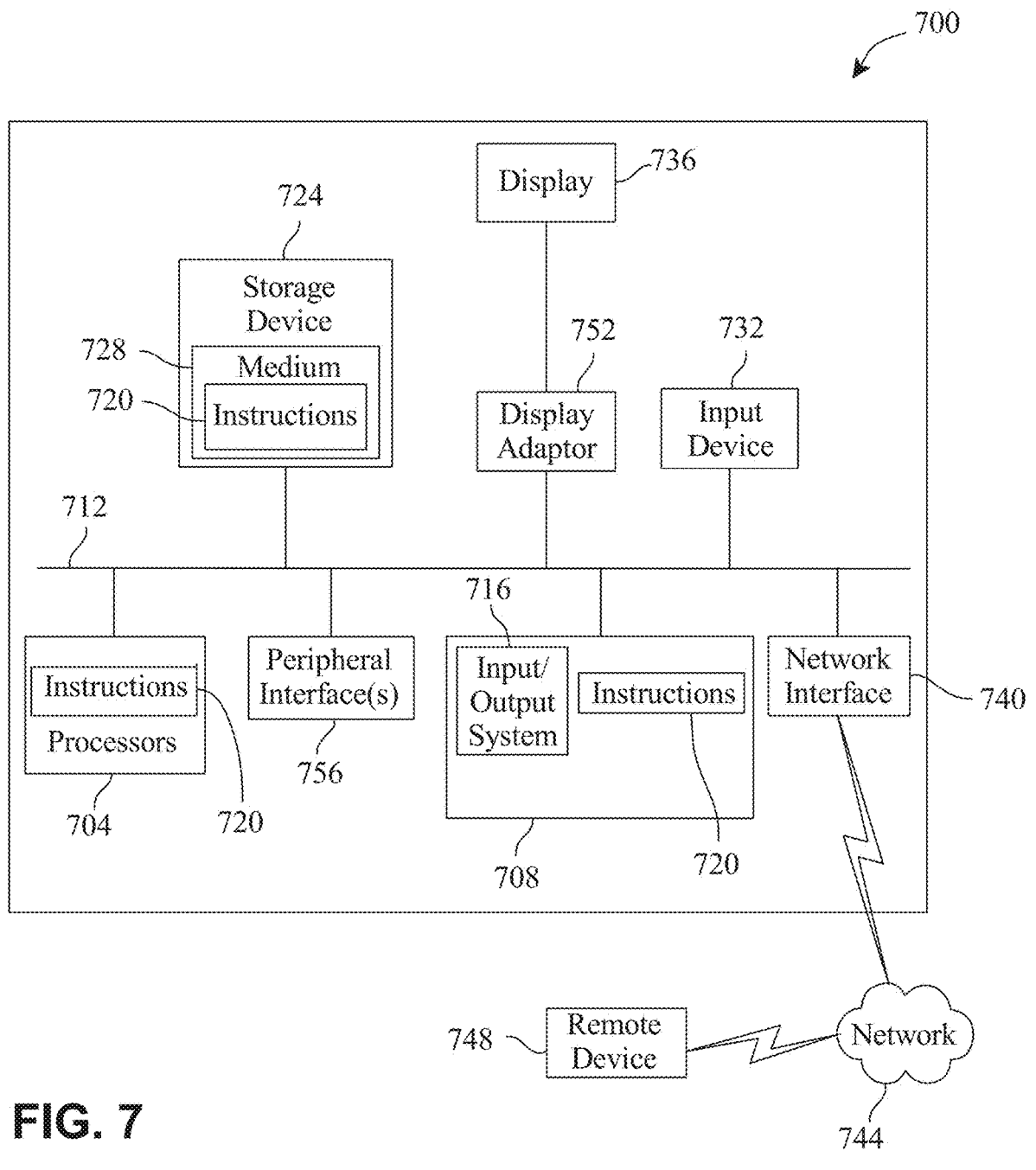
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display 736. Examples of a display device include, but are not limited to, a liquid crystal display (LCD), a cathode ray tube (CRT), a plasma display, a light emitting diode (LED) display, and any combinations thereof. Display adapter 752 and display 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an updated terminal node projection, wherein the system comprises:

at least a processor; and a memory communicatively connected to the at least a processor, wherein the memory contains instructions configuring the at least a processor to:

receive a plurality of datasets, wherein each dataset of the plurality of datasets comprises information associated with a patient and information associated with admission criteria and wherein each dataset of the plurality of datasets is associated with a terminal node representative of an admission outcome;

identify a terminal node projection predicting the admission outcome for each patient as a function of the plurality of datasets, wherein identifying the terminal node projection comprises classifying each dataset of the plurality of datasets using a natural language processing model and historical data of previous patient admissions, wherein classification of each dataset of the plurality of datasets generates embeddings related to each dataset of the plurality of datasets;

generate an entry criteria set as a function of the terminal node projection, wherein generating the entry criteria set comprises generating a ranking module configured to rank a weight of the entry criteria set, wherein the ranking module is further configured to assign a weight to each entry criterion of the entry criteria set, and wherein the weight is determined as a function of a severity of each entry criterion of the entry criteria set;

train a machine-learning model to generate terminal node projections as a function of the embeddings in order to increase an accuracy of terminal node projections generated by the machine-learning model; and generate an updated terminal node projection as a function of the trained machine-learning model, the entry criteria set, and the plurality of datasets.

2. The system of claim 1, wherein generating the entry criteria set as a function of the terminal node projection comprises generating the entry criteria set using an additional machine-learning model trained using a training data set configured to correlate the plurality of datasets to the entry criteria set.

3. The system of claim 1, wherein generating the updated terminal node projection as a function of the trained machine-learning model, the entry criteria set, and the plurality of datasets comprises:

training the machine-learning model using a training data set configured to correlate the entry criteria set to the terminal node.

4. The system of claim 1, wherein the plurality of datasets comprises patient cohort data.

5. The system of claim 1, wherein the terminal node projection comprises a determination of a classification process.

6. The system of claim 1, wherein the entry criteria set comprises a medical diagnosis.

7. The system of claim 1, wherein:

the entry criteria set comprises a plurality of weights; and generating the entry criteria set as a function of the terminal node projection comprises ranking the plurality of weights using the ranking module.

8. The system of claim 7, wherein the ranking module comprises a supervised machine learning model trained using the historical data.

9. The system of claim 7, wherein the ranking module is configured to generate an ordered hierarchy based on a relative importance of each criterion of a plurality of criteria within the entry criteria set.

10. The system of claim 1, wherein the terminal node projection is identified using a predictive categorization as a function of recurring patterns within the embeddings related to each dataset of the plurality of datasets.

11. A method for terminal node optimization, wherein the method comprises:

receiving, by at least a processor, a plurality of datasets, wherein each dataset of the plurality of datasets comprises information associated with a patient and information associated with admission criteria and wherein each dataset of the plurality of datasets is associated with a terminal node representative of an admission outcome;

identifying, by the at least a processor, a terminal node projection predicting the admission outcome for each patient as a function of the plurality of datasets, wherein identifying the terminal node projection comprises classifying each dataset of the plurality of datasets using a natural language processing model and historical data of previous patient admissions, wherein classification of each dataset of the plurality of datasets generates embeddings related to each dataset of the plurality of datasets;

generating, by the at least a processor, an entry criteria set as a function of the terminal node projection, wherein generating the entry criteria set comprises generating a ranking module configured to rank a weight of the entry criteria set wherein the ranking module is further configured to assign a weight to each entry criterion of the entry criteria set, wherein the weight is determined as a function of a severity of each entry criterion of the entry criteria set;

training, by the at least a processor, a machine-learning model to generate terminal node projections as a function of the embeddings in order to increase an accuracy of terminal node projections generated by the machine-learning model; and generating, by the at least a processor, an updated terminal node projection as a function of the trained machine-learning model, the entry criteria set, and the plurality of datasets.

12. The method of claim 11, wherein generating the entry criteria set as a function of the terminal node projection comprises generating the entry criteria set using an additional machine-learning model trained using a training data set configured to correlate the plurality of datasets to the entry criteria set.

13. The method of claim 11, wherein generating the updated terminal node projection as a function of the trained machine-learning model, the entry criteria set, and the plurality of datasets comprises:

training a machine-learning model using a training data set configured to correlate the entry criteria set to the terminal node.

14. The method of claim 11, wherein the plurality of datasets comprises patient cohort data.

15. The method of claim 11, wherein the terminal node projection comprises a determination of a classification process.

16. The method of claim 11, wherein the entry criteria set comprises a medical diagnosis.

17. The method of claim 11, wherein:

the entry criteria set comprises a plurality of weights; and generating the entry criteria set as a function of the terminal node projection comprises ranking the plurality of weights using the ranking module.

18. The method of claim 17, wherein the ranking module comprises a supervised machine learning model trained using the historical data.

19. The method of claim 17, wherein the ranking module is configured to generate an ordered hierarchy based on a relative importance of each criterion of a plurality of criteria within the entry criteria set.

20. The method of claim 11, wherein the terminal node projection is identified using a predictive categorization as a function of recurring patterns within the embeddings related to each dataset of the plurality of datasets.

* * * * *